(12) United States Patent
Wong et al.

(10) Patent No.: US 8,316,705 B2
(45) Date of Patent: Nov. 27, 2012

(54) MONITORING THE STRUCTURAL HEALTH OF COMPONENTS

(75) Inventors: Albert Wong, Toorak (AU); Kelly Ann Tsoi, Fishermans Bend (AU); Paul Rawson, Altona Meadows (AU); Dave Wynne, Bentleigh (AU)

(73) Assignee: The Commonwealth of Australia, Canberra, Australian Capital Territory (AU)

( * ) Notice: Subject to any disclaimer, the term of this patent is extended or adjusted under 35 U.S.C. 154(b) by 350 days.

(21) Appl. No.: 12/527,031

(22) PCT Filed: Feb. 14, 2008

(86) PCT No.: PCT/AU2008/000193
§ 371 (c)(1),
(2), (4) Date: Feb. 11, 2010

(87) PCT Pub. No.: WO2008/098301
PCT Pub. Date: Aug. 21, 2008

(65) Prior Publication Data
US 2010/0162808 A1     Jul. 1, 2010

(30) Foreign Application Priority Data
Feb. 14, 2007   (AU) ................................ 2007900736

(51) Int. Cl.
*G01M 13/02* (2006.01)
(52) U.S. Cl. .......................................................... 73/162
(58) Field of Classification Search ........................ None
See application file for complete search history.

(56) References Cited

U.S. PATENT DOCUMENTS

| | | | |
|---|---|---|---|
| 5,210,704 A * | 5/1993 | Husseiny | 702/34 |
| 6,059,500 A | 5/2000 | Dirmeier et al. | |
| 2004/0075565 A1 | 4/2004 | Bennett | |
| 2006/0154046 A1 | 7/2006 | Takahashi et al. | |

FOREIGN PATENT DOCUMENTS

| | | |
|---|---|---|
| JP | 61-86629 A | 5/1986 |
| JP | 2007-262840 A | 10/2007 |
| RU | 2168724 C1 | 6/2001 |
| WO | 2006/128258 A1 | 12/2006 |

OTHER PUBLICATIONS

International Search Report: dated Apr. 14, 2008; PCT/AU2008/000193.

* cited by examiner

*Primary Examiner* — Andre Allen
(74) *Attorney, Agent, or Firm* — Ladas & Parry LLP (57) ABSTRACT

The present invention relates to a system for monitoring the health of mechanical and structure components of a machine. For example, the present invention is capable of monitoring the operational integrity of critical components of critical components of an aircraft such as the gearbox of a helicopter. The present invention is based on the principle of detecting a traceable substance when the substance is released from the component being monitored in the event of predetermined condition being satisfied, such as exceeding the operational temperature of the component, or a fault in the component occurring, such as a crack being formed.

33 Claims, 6 Drawing Sheets

MONITORING THE STRUCTURAL HEALTH OF COMPONENTS

FIELD AND BACKGROUND OF THE INVENTION

The present invention relates to a system and method for monitoring the structural health of mechanical components or structural components. For example, the present invention can be used to monitor, but by no means exclusively, the structural health of critical components of a gearbox of a helicopter.

Under normal operations, the maintenance of aircraft is usually performed on a routine basis according to a strict schedule based on hours of operation. Scheduled maintenance has proven successful in most cases. In the case of other mechanical platforms, scheduled maintenance also allows for regular inspection of susceptible components. However, there are situations where benefits can be obtained by initiating maintenance actions based on the monitored health of the components. The first is that of condition-based maintenance which for some components can deliver cost savings by eliminating unnecessary maintenance actions. Secondly, fixed period scheduled maintenance does not always catch all potential faults, and a small number of rogue faults could develop into failures between overhauls. For example, for certain safety-critical components such as a helicopter gearbox, this could lead to the total loss of the aircraft.

A diagnostic technique such as wear debris analysis has been used to help identify damage, cracking or wear of components in need of replacement. More particularly, wear on mechanical components usually creates debris that can be detected and analysed to identify its origin. However, a difficulty in relying on debris analysis is that debris may remain undetected when trapped within various niches of a mechanical system. Excessive debris that remains undetected could also cause collateral damage to other components of the system. Another problem with the reliance on the detection of wear debris is that some faults, such as cracking, do not generate much (or any) debris until catastrophic failure is imminent, thus making the technique not useful against such modes of failure.

Another diagnostic technique involves vibration analysis of components. However, vibration analysis is generally less successful than debris analysis because a bearing fault often produces little or no discerning vibration.

It has been recognised that a precursor to a complete mechanical failure of bearings and/or gears is over heating, stress fractures or deformation of the components. A risk that is inherent with current practices is that the precursors or telltale signs of a mechanical failure may go unnoticed during routine maintenance or that there may be failure in the period between scheduled servicing. As a result, despite the most vigilant maintenance schedules, complete mechanical failure can, and still does, occur which can lead to unscheduled downtimes, expensive replacement of machinery and/or components or, in the case of aircraft, a loss of life.

It is therefore an object of the present invention to devise an alternative means for monitoring the mechanical health of mechanical components that can complement existing maintenance practices.

SUMMARY OF THE INVENTION

According to the present invention, a system for monitoring the wear, fatigue failure, or structural health of a mechanical or structural component is provided; the system includes:

a) one or more chambers directly or indirectly connected to the component or incorporated in the structure of the component, wherein the or each chamber contains a traceable substance and, in use, at least one of said chambers is ruptured or opened so as to allow the traceable substance to be discharged therefrom when either one or a combination occurs: i) a predetermined operating condition of the component is satisfied or ii) a structural failure of the component (or some level of structural failure of the component) causes the chamber to be opened or ruptured; and b) a detector device or a means for detecting the traceable substance which has been discharged from at least one of the chambers.

An advantage provided by the present invention is that as soon as the traceable substance is detected, operation of the component can be monitored closely and, if required, stopped to allow investigation and/or servicing.

It is envisaged that the present invention may be used in a wide range of different applications such as the drive mechanism of vehicles and aircraft, machinery with mechanical components susceptible to fatigue damage or other structural faults and which, if failure of the components occur, could lead to expensive replacement of parts, downtime and/or, in the worst case, physical injury or death of personnel. For example, the present invention may have particular application, although by no means exclusively, to monitor the fatigue damage and/or faults on critical mechanical components such as a bearing or gear in the gearbox of a helicopter. In yet another example, the present invention may be used to monitor the structural health of fixed wing aircraft.

The chamber(s) connected to the component may be made in any suitable form and be made from any suitable material.

In an embodiment, the traceable substance is caused to be released from the chamber(s) without hindering the continuous operation of the apparatus. It is also possible for release of the traceable substance to co-inside with the component sustaining a high level of structural failure that causes the component to become inoperative.

In an embodiment, the traceable material is preloaded into the chambers before being ruptured or opened.

In an embodiment, the chambers are sealed chambers prior to release of the traceable substance. In other words, the traceable substance is confined to the chamber(s) prior to being ruptured or opened and is not a material that is consumed during the normal operation of the component such as fuel.

In an embodiment the predetermined operating condition is the operating temperature of the component and the traceable substance is released when the operating temperature of the component substantially equals or exceeds a threshold value. In other embodiments, the predetermined operating condition may be operational vibrations, stresses and strains in the components, loads on the component, or chemical substances exposed to the component.

In an embodiment the structural failure of the component causes the chamber to be breached thereby releasing the traceable substance, for example, the chamber is breached when a structural failure such as a crack is formed in the component. In other embodiments the structural failure may be in the form of bending or deformation of the component. A specific example is when one of the chambers of the present invention is mounted or connected to a bearing race and the chamber is crushed or ruined as a result of an impact with the bearing race. Other examples of the chamber being breached include when the chamber has eroded or corroded. In each of the above examples, the traceable substance is released when the structural integrity of the component is to some extent compromised or not preserved.

In the situation where the traceable substance is discharged from one of said chambers when a crack is formed in the component, the crack then provides a passageway through which the traceable substance can be discharged from the chamber. In other words, in the situation where the crack develops or grows from the chamber to an outer surface of the component, the chamber and the surrounding are bridged, thus allowing the traceable substance to be released and be detected. In this situation the chamber is at least defined or formed by the component and structural failure of the component causes the rupturing or opening of the chamber.

When a series of the chambers discharge the traceable substance as a result of the formation of the cracks, in an embodiment that the chambers be located at different positions and contain different types of traceable substance so that detection of a particular type of traceable substance represents a particular stage of crack growth. An advantage provided by this aspect of the present invention is that chambers can be strategically located across the component and detection of the traceable substance contained in the chambers can provide a prognostic capability as it permits a means for tracking the progression of the fatigue damage.

In an embodiment a series of the chambers are located adjacent to load bearing surfaces or surfaces that are contacted by other co-operating mechanical components. Moreover, the chambers may be located at any potential site at which structural failure of the component it a risk.

For instance, in the case where the system is being used to monitor the wear on a cog or gear, it is preferred that the chambers be located immediately adjacent to the meshing surfaces of the teeth of the cog. Cracks or material removed by wear can form bridging of the chamber and the external environment, thus allowing the traceable substance to be discharged and detected.

In the situation where the traceable substance is discharged from a chamber when the temperature of the component equals or exceeds a threshold value, in an embodiment the chamber(s) include a frangible section that is temperature dependent and has a softening point so that when the operating temperature of the component equals or exceeds the softening point of the frangible section, the frangible section gives way and thereby allows the traceable material to be discharged.

In the situation where a series of said chambers release a traceable substance when the temperature of the component equals or exceeds a threshold value, it is preferred that the traceable substance contained within at least two of the chambers have different properties and that the chambers be adapted so that the traceable material be discharged at different operating temperatures. An advantage provided by this preferred aspect of the present invention is that the release of different types of traceable substances will occur in a stage wise manner as the operating temperature of the component increases thereby enabling the rate of the change in temperature of the component to be monitored.

In an embodiment the chamber(s) are defined by two or more wall sections joined together and that the frangible section be a frangible adhesive used to join the sections.

The frangible adhesive may be any suitable material such as a polymeric based material, or a metallic material such as solder.

In an embodiment the chambers are formed by two strips of suitable material that are joined together, and at least one of the strips have a recess that contains the traceable substance.

In an embodiment the frangible adhesive has a softening point at a temperature range suitable to the application.

In the situation where the traceable substance is discharged from a chamber when the temperature of the component equals or exceeds a threshold value, it is possible for some other form of failure mechanism to cause the traceable substance to be discharged. For example, the failure mechanism may be, but is by no means limited to: i) thermal expansion of the traceable substance causing the traceable substance to expand beyond a volume defined by the chamber, which in turns causes the chamber to be ruptured; ii) relative movement between the chamber and the component causing rupture; and iii) any form of failure of the material defining the chamber(s).

It will be appreciated that the hardware component may include, but is by no means limited to: a cog, gear, bearing, drive shaft, cam surface, cylinder or cylinder head, wing, or any other mechanical and structural component of a fixed or rotary wing aircraft. In the situation where the component is a structural component of an aircraft or some other external component of an apparatus it is envisaged that the means for detecting the traceable substance may involve any suitable form of mechanical, electrical, physical or chemical analysis of the atmospheric environment.

An example of an open system in which the present invention may have application is when the component being monitored is in the form of blades of a gas turbine engine. Turbine blades are conventional manufactured with an internal chamber. The internal chamber may be adapted so as to contain the traceable substance when the structural integrity of the blades is compromised, for example by a crack bridging between the internal chamber to the outer face of the blade, the traceable substance may be detected.

However, in a large number of applications, it is envisaged that the component will be an internal component of an apparatus and accordingly, in an embodiment the system includes a housing that at least partially encloses the component and the means for detecting the traceable substance is adapted to detect the presence of the traceable substance in the housing. For example, when the mechanical hardware component is a cog, gear or bearing that forms part of a gearbox, the housing may be the housing of the gearbox, and the environment in which the traceable substance is released may be the lubrication medium.

In an embodiment, the mass of the traceable material or volume of the chambers is significantly less than the mass or volume of the component being monitored. Typically, the volume or mass of the traceable substance is less than 10% of the volume or mass of the component. However this need not necessary be the case, for example, in the situation where the traceable substance is preloaded into an internal chamber of the turbine blade of a gas turbine, the volume or mass of the traceable could be greater than 10% of the volume or mass of the turbine blade itself.

Although the means for detecting the traceable substance may be in any form, such as a window for allowing the presence of the traceable substance to be optically detected, in an embodiment said detector device can carry out chemical spectral analysis to identify the presence of the traceable substance.

In the situation where the mechanical component is enclosed in the housing, if the mechanical component is exposed to a lubricant during normal operation, the traceable substance can be discharged into the lubricant and the means for detecting the traceable substance be able to identify the presence of the traceable substance in the lubricant.

Furthermore, in an embodiment the spectral analysis is undertaken in an appropriate wavelength range as the visible characteristics of the lubricant are often affected by its degradation.

In the situation where the mechanical component has a series of chambers containing traceable substances of different properties and the chambers are located at various sections of the component, in an embodiment the detector device for detecting the traceable substance has a capacity to distinguish between different types of traceable substances, and in turn, enable the section of the component from which the traceable substance has been released to be identified. Typically, the means for detecting the traceable substance can be calibrated so as to identify when the traceable substance is released and trigger an output signal that identifies the section of the component from which the traceable substance has been released.

In addition in the situation where the system of the present invention includes multiple components that are being monitored, in an embodiment the chamber(s) associated with each component contain a different traceable substance and the detector device for detecting the traceable substance be able to differentiate between the different types of traceable substance, and in turn, enable the mechanical component from which the traceable substance has been released to be identified. An advantage provided by this preferred aspect of the present invention is that damage in the form of overheating or cracking of each component can be monitored by detecting the particular traceable substance associated with each component.

The traceable substance may be in any suitable form including chemical substances such as a paint, dye or gas. The traceable substance may also be of any state including a paste, granule or some other form of solid material depending on the operating temperature.

In an embodiment the dye may be an alkyl modified naphthalocyanine, polyene, polymethine, squaryluim, croconium, iminium salt, triphenylmethane or metal dithiolene class of compound that is suitably soluble in oil. The traceable substances may also include oxides of nitrogen, fluorescing compounds, radioactive materials, or any material not normally found in the system that may be preferentially detected.

In an embodiment the dye is vanadyl-2,11,20,29-tetra-tert-butyl-2,3-naphthalocyanine. This dye is particularly suitable for use in situations where the component being monitored is a petroleum or synthetic based oil and the dye will be mixed with the oil when discharged. One of the characteristics of the oil is that dye absorbs in the Near Infrared region which is outside of the UV visible spectra obscured by the synthetic turbine oil. The presence of the dye can therefore be readily and continuously monitored using spectral analysis.

To increase the solubility of the dye, in an embodiment the system includes a co-solvent that will maximise its rate of discharge and mixing into the lubrication oil once a fault develops. In other words, the co-solvent increases the solubility and miscibility of the traceable substance in lubricants. In an embodiment the solvent used with the above mentioned dye is biphenyl.

According to the present invention there is provided a hardware component that is configured such that this component includes one or more chambers directly or indirectly connected to the mechanical component or incorporated into the structure of the component, such as a bearing, wherein the or each chamber contains a traceable substance and, in use, at least one of said chambers is ruptured or opened so as to allow the traceable substance to be discharged therefrom when either one or a combination of the following occurs i) a predetermined operating condition of the component is satisfied or ii) a structural failure of the component (or some level of structural failure of the component) causes the chamber to be opened or ruptured.

An advantage of the hardware component, according to the present invention, is that detection of the traceable substance will allow early detection of damage so that suitable precautions and servicing of the mechanical component can be carried out to prevent the mechanical component from failing.

In the event that the chamber is fractured and traceable substance discharged, the traceable substance can be detected using any suitable means. For example, detection may be carried out by using any form of chemical or physical detection means and in the situation when the traceable substance has an odour, the detection means may even be provided by a trained sniffer dog or some other animal.

The mechanical component may also include any one or a combination of the preferred features of the system of the present invention described above.

According to the present invention there is also provided a method for monitoring the damage/structural health of a component of a mechanical or structural system, the component including one or more chambers directly or indirectly connected to the component or incorporated in the component, wherein the or each chamber contains a traceable substance and, in use, the or each chamber is ruptured or opened so as to allow the traceable material to be discharged therefrom without hindering the continuous operation of the component when either one or a combination of the following occurs i) a predetermined operating condition of the component is satisfied or ii) a structural failure of the component (or some level of structural failure of the component) causes the chamber to be opened or ruptured, and the method including detecting the presence of a traceable substance released from the mechanical hardware component.

The component of the method of the present invention may also include any one or a combination of the preferred features described above.

BRIEF DESCRIPTION OF THE DRAWINGS

The present invention will now be described with reference to a series of embodiments illustrated in the accompanying figures, of which.

DETAILED DESCRIPTION

Figure 1:
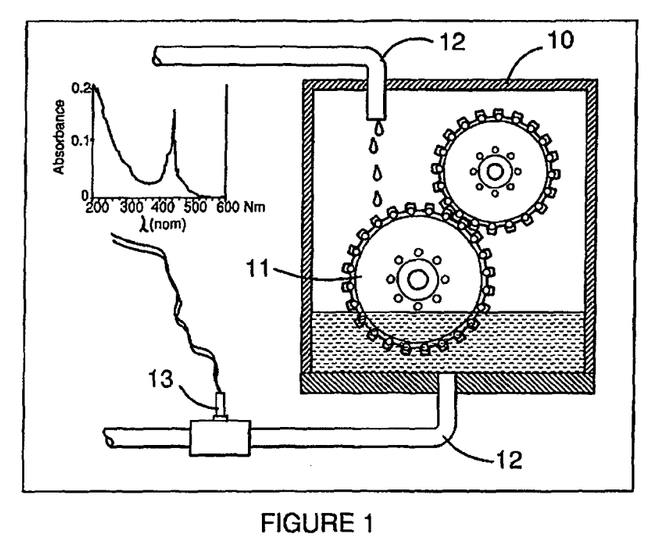
FIG. 1 is a schematic drawing of a system according to an embodiment of the present invention including two intermeshing gears enclosed in a housing that are lubricated with an oil and a detector for detecting the presence of a traceable substance in the oil.

The system of the present invention as shown in FIG. 1 includes a housing 10 enclosing gears that require monitoring. The components of the gearbox are lubricated by oil that is circulated through piping 12 and past a detector 13 in the form of a spectral analyser.

The system of the present invention can be used for monitoring the damage/structural health of mechanical components such as gears, cogs, drive shafts and bearings of any components of a mechanical apparatus.

Figure 2:
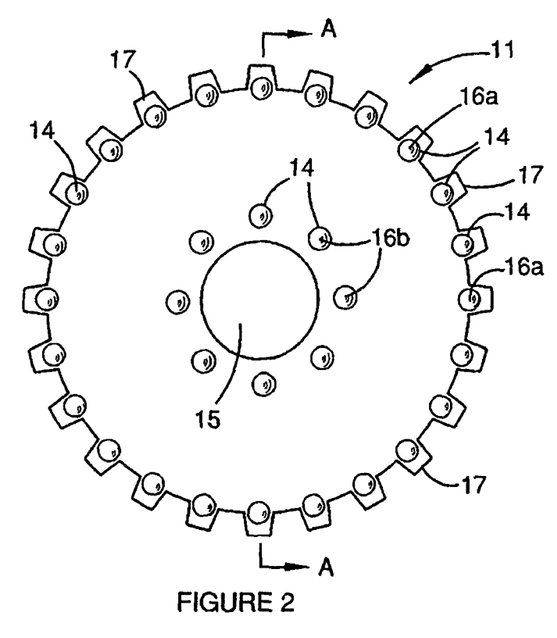
FIG. 2 is a detailed front view of the gear shown in FIG. 1 according to an embodiment of the present invention.
Figure 3:
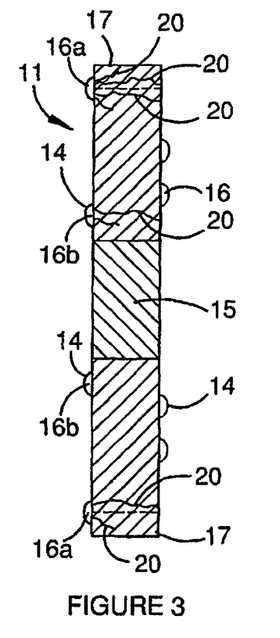
FIG. 3 is a cross-sectional side view along the line A-A of the gear shown in FIG. 2.

FIG. 2 illustrates the front view of a gear 11 commonly found in the gearbox of a vehicle such as a helicopter comprising a series of teeth 17 that intermesh with the teeth of another gear. Attached to the exterior face of the gear is a series of domed shaped shells 14 that, together with the main body, of the gear 11, define chambers 16 containing a traceable substance that is soluble in the lubricating oil. As can be seen in FIGS. 2 and 3, the chambers 16a are located so as to overlap the base of each tooth 17. A series of chambers 16b are located adjacent to the central axis 15 of the gear. The purpose of the chambers 16 is to define a void containing a traceable substance that is in direct contact with portions of the gear that are prone to cracking. During operation of the gear, crack growth 20 occurs under the chambers which provides a passageway through which the traceable substance can be discharged into the lubricating oil. The detector 13, using a technique of spectral analysis, continuously monitors for the presence of the traceable substance in the oil.

The graph shown in FIG. 1 illustrates an example of the output of the detector 13 and the presence of the traceable substance is indicated by the peak in the graph at a wavelength of approximately 440 nm.

As can best be seen in FIG. 3, crack growth 20 formed in the gear extends from the walls or face of the gear which forms part of the chamber to an external surface, and thereby provides a passageway for the traceable substance to be discharged.

Figure 4:
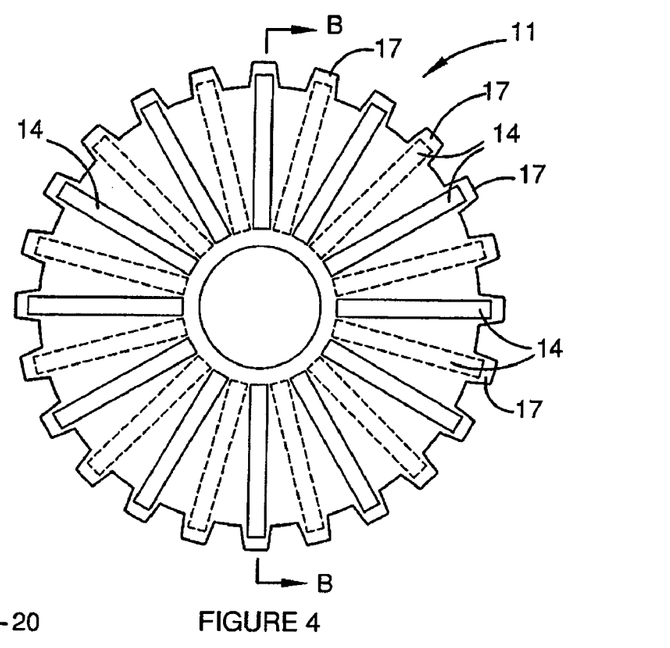
FIG. 4 is a detailed front view of a gear according to an alternative embodiment of the present invention.
Figure 5:
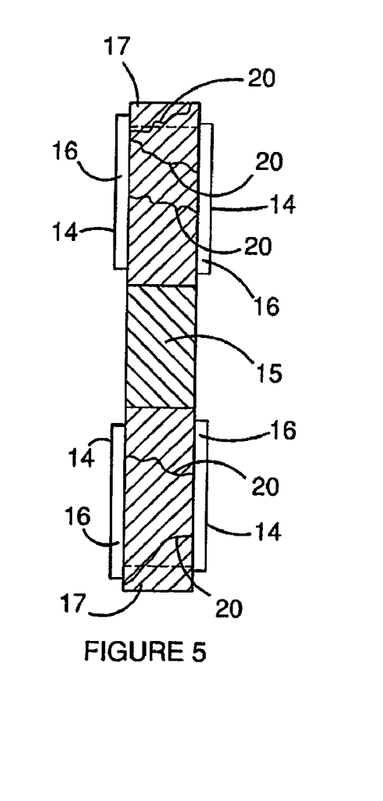
FIG. 5 is a cross-sectional side view along the line B-B of the gear shown in FIG. 4.

FIGS. 4 and 5 illustrate an alternative embodiment of a gear according to the present invention wherein the chambers 16 are formed by elongated shells 14 containing a traceable substance. In particular, the chambers 16 extend outwardly from a central axis 15 of the gear toward each tooth 17 and are located on both sides of the gear and on alternating teeth 17 so that the gear is dynamically balanced.

As can be seen in FIG. 5, cracks formed in the face of the gear underneath the elongated shells 14 and extending to an external surface form a passageway that allows the traceable substance to be discharged into the lubricating oil.

Figure 6:
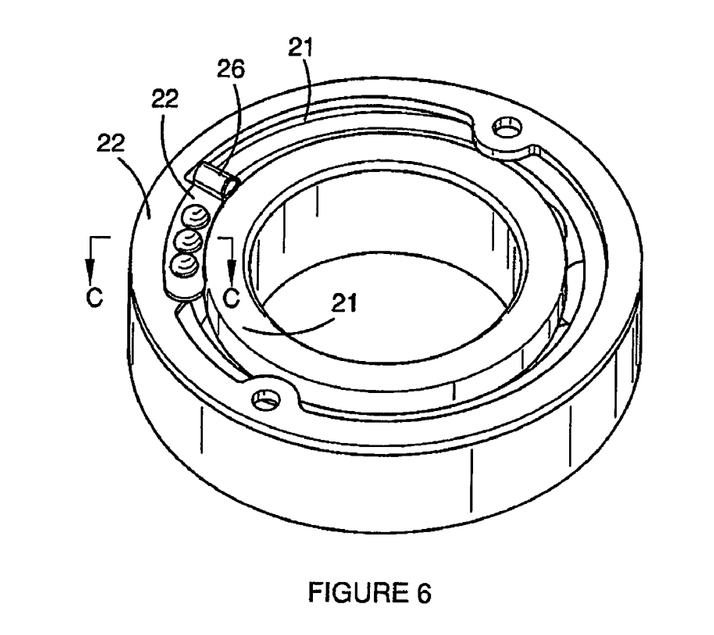
FIG. 6 is a perspective view of yet another alternative embodiment of the present invention including a bearing race.
Figure 7:
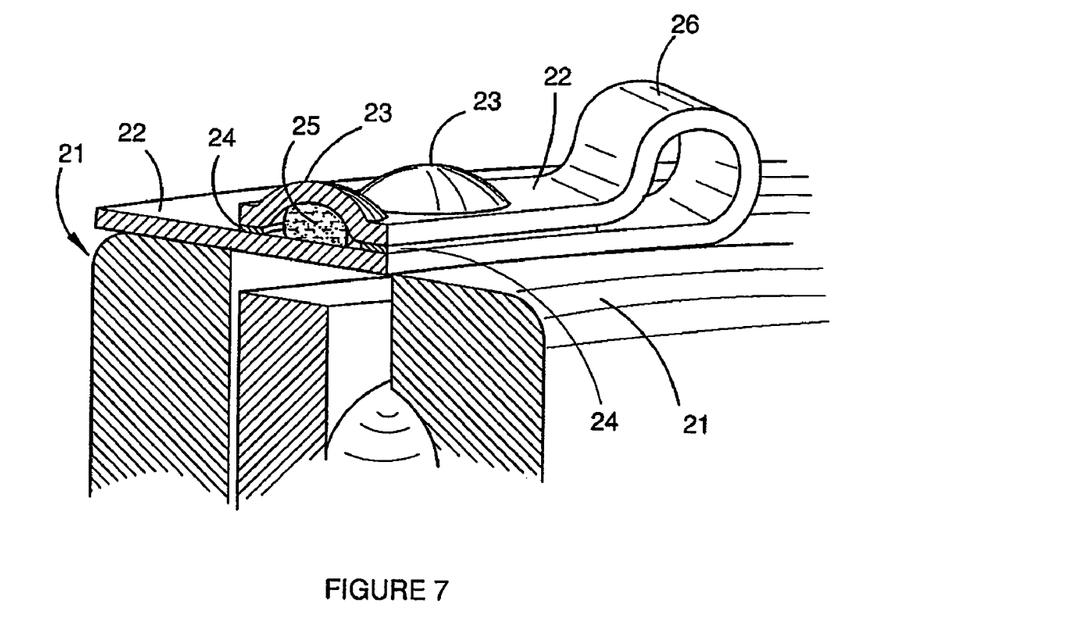
FIG. 7 is a cross-sectional view along the line C-C of the bearing race shown in FIG. 6.

FIGS. 6 and 7 illustrate yet another embodiment of the present invention in which the mechanical component being monitored is a set of bearings inside of bearing race 21. The bearing race 21 is fitted with three chambers 16 defined between two sheets of foil 22 hinged together by looped portion of foil 26. One of the sheets of foil has had a dome 23 pressed therein which contains the traceable substance 25 and the sheets 22 are soldered around their perimeter using a solder 24 having a known softening or melting point.

Figure 8:
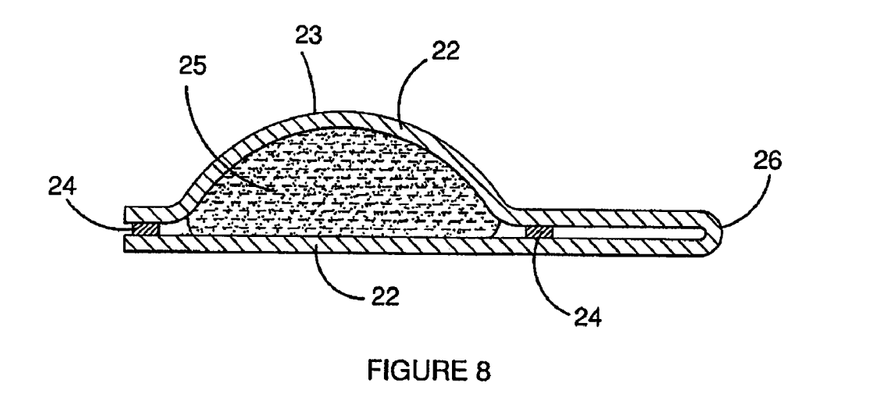
FIGS. 8 and 9 schematically illustrate a chamber of the embodiment shown in FIGS. 6 and 7 in which the chamber is in closed sealed configuration and a fractured open configuration respectively.
Figure 9:
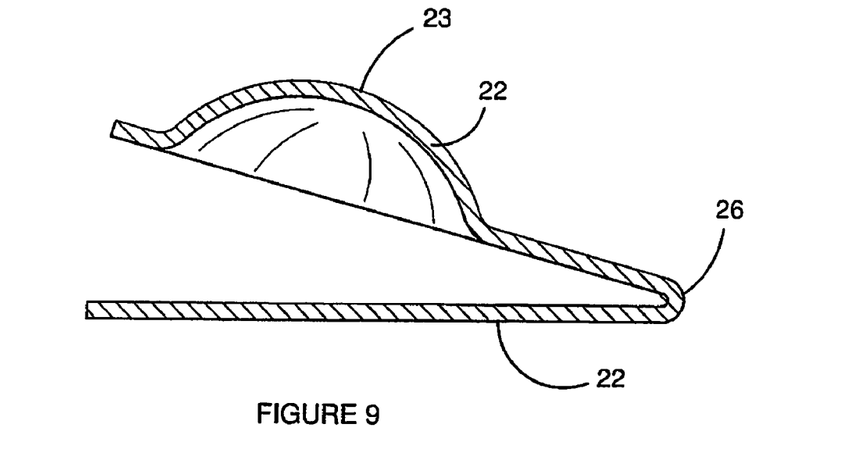

In the event that the operating temperature of the bearing race 21 exceeds the softening point of the solder 24, the solder will melt/soften and allow the traceable substance 25 to be discharged. In other words, the embodiments shown in FIGS. 8 and 9 provide a means for detecting when the operating temperature of the bearing race 21 reaches the softening point of the solder. The softening point of most solders is well defined and it is possible to obtain solders having different softening points. Therefore, in the situation where a number of chambers are used, it is possible to use solders having varying softening point and to place a traceable substance having particular properties in each chamber so that when the traceable substance has been discharged and detected, it will be possible to establish a temperature profile for the component during operation.

FIGS. 8 and 9 schematically illustrate one of the chambers of the embodiment shown in FIGS. 6 and 7. Specifically, FIG. 8 illustrates the embodiment in which the chamber is sealed by solder and FIG. 9 illustrates and embodiment in which the solder has been softened and the chamber opened.

In applications where the system is used to monitor the mechanical health of intermeshing gears and bearings that are lubricated by oil in a housing, the most appropriate traceable substance 25 is an oil soluble dye. The solubility of the dye must be such that the dye can transfer through a small developing crack in the chamber enclosing the dye. Ideally, the dye should be able to be completely and rapidly discharged into the oil and be thermally stable over a broad range of temperatures. In addition, for ease of manufacture the dye is preferably a solid phase at room temperature which can be moulded, extruded or otherwise formed into a desired shape suitable for encapsulation.

In order to meet the objectives, we have selected a dye and co-solvent combination. The dye we have found that best meets our requirements is an alkyl modified naphthalocyanine. More specifically, the best performing dye is vanadyl-2,11,20,29-tetra-tert-butyl-2,3-naphthalocyanine when used in combination with a biphenyl solvent that can be added to the lubricating oil. This particular dye absorbs in the Near Infrared region. In contrast, synthetic turbine oil absorbs in the UV visible region and, therefore, the presence of the dye in the oil can be readily detectable using conventional spectral analysis equipment. The spectral analysis can be carried out on a routine periodic or continuous basis.

Trials

Trial 1

Figure 10:
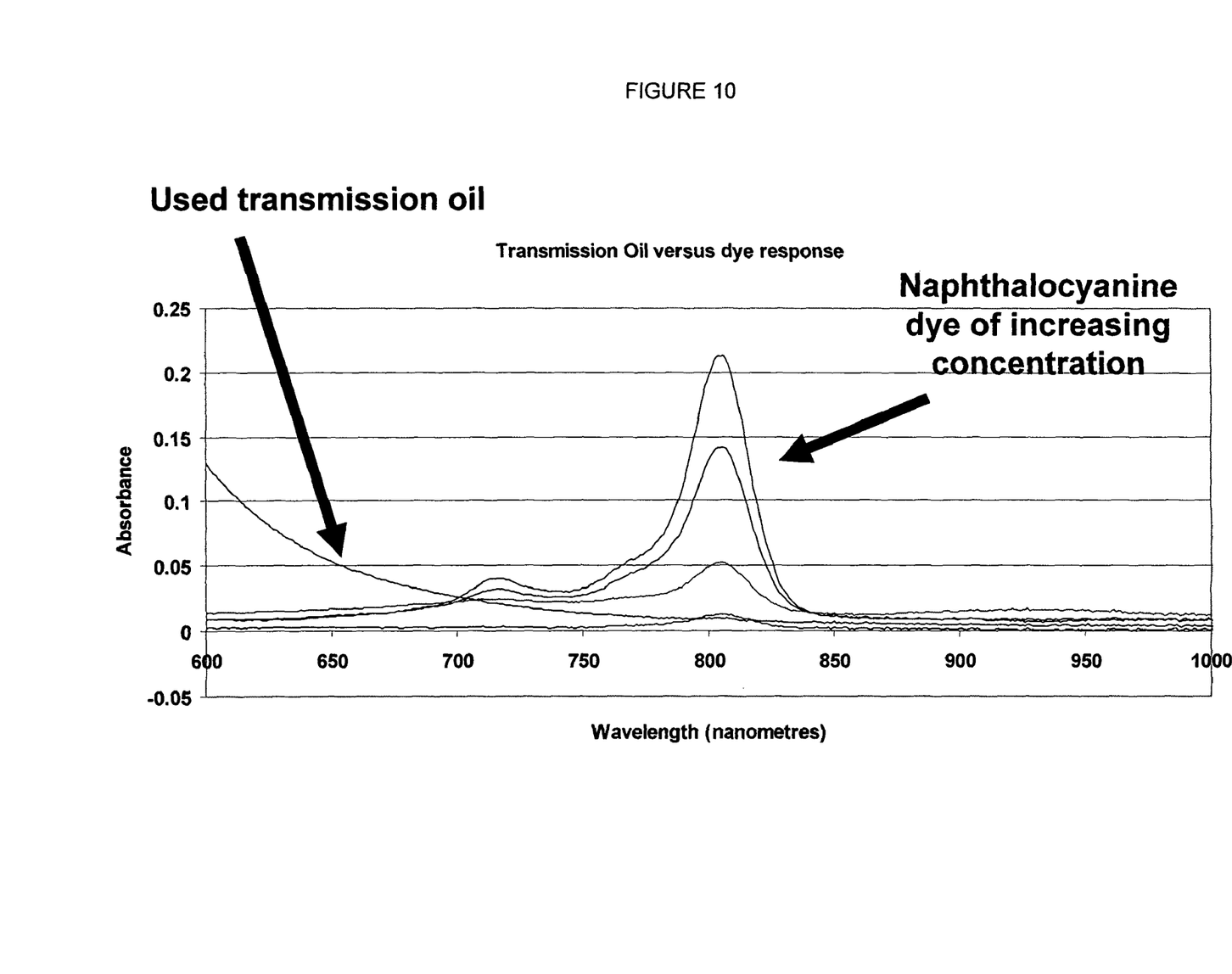
FIG. 10 is a graph illustrating the results of a trail using a bearing race as shown in FIGS. 6 and 7, the results of the trial are recorded in the graph in terms of absorbance versus wavelength of a spectral analyser.

This trial involved the use of a bearing race substantially in accordance with bearing race shown in FIGS. 6 and 7. The chambers of the bearing race contained a dye in the form of vanadyl-2,11,20,29-tetra-tert-butyl-2,3-naphthalocyanine in combination with a biphenyl co-solvent. The bearing race was submerged in a bath of used transmission oil and the chamber stressed until the chambered ruptured. The graph shown in FIG. 10 illustrates the results of a spectral analyser used to scan the oil for the dye. The results are presented in terms of absorbance versus wavelength.

As can be seen from the graph, the transmission oil provided an absorbance of between 0.1 and 0.15 at about 600 nm, whereas the dye demonstrated an absorbance at approximately 800 nm. As the dye was progressively released from the chamber, the spectral analyser detected the presence of the dye at four different levels, each shown in FIG. 10 by a separate line. Higher concentrations of the dye in the oil had higher absorbance rate at 800 nm.

Trial 2

Figure 11:
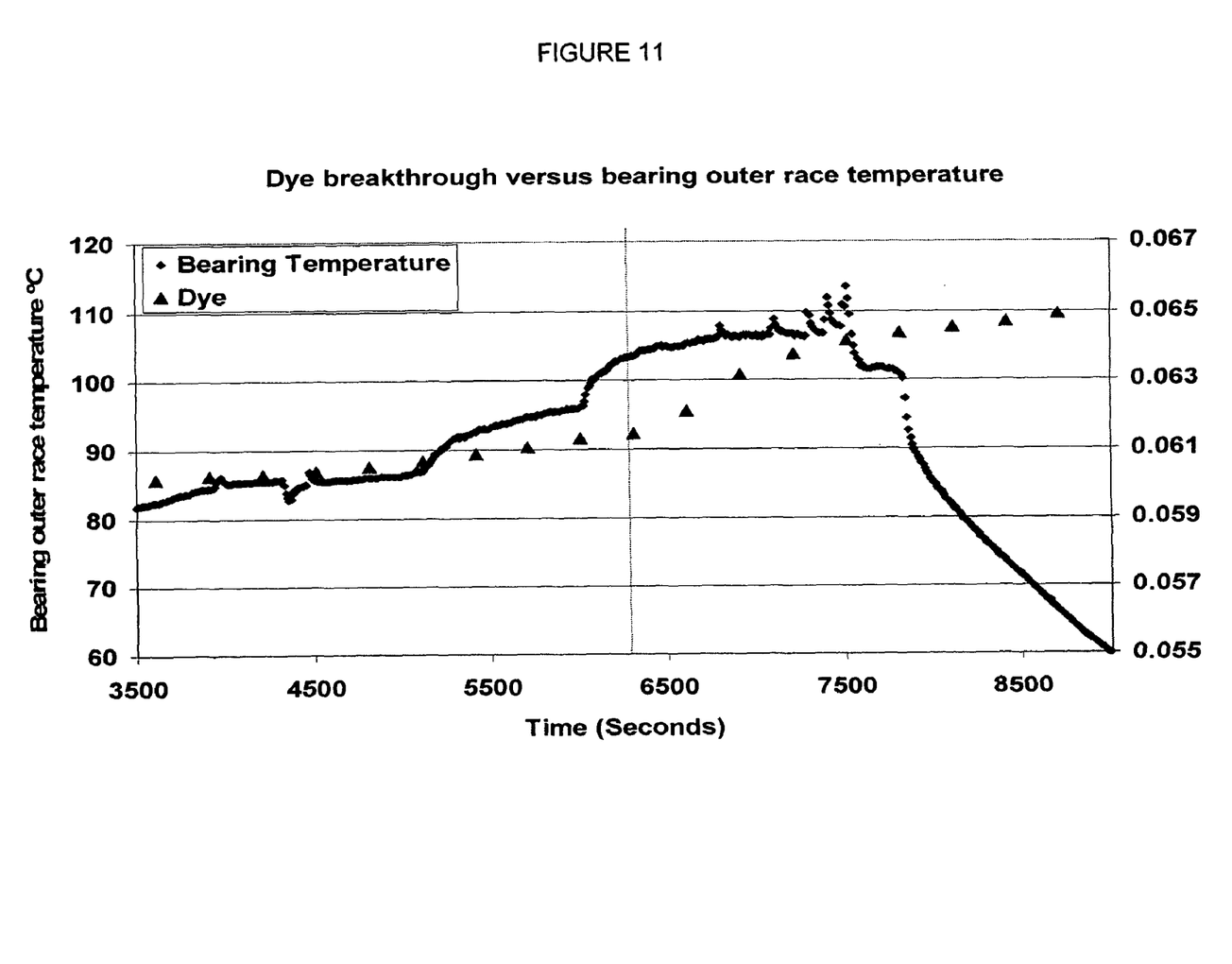
FIG. 11 is a graph illustrating the results of a trail using a bearing race as shown in FIGS. 6 and 7, the results of the trial are recorded in the graph in terms of absorbance levels and operating temperature of the bearing race.

This trial involves the use of a bearing race substantially in accordance with bearing race shown in FIGS. 6 and 7. The chambers of the bearing race contained a dye in the form of vanadyl-2,11,20,29-tetra-tert-butyl-2,3-naphthalocyanine in combination with a biphenyl co-solvent. The bearing race was also fitted with a thermocouple and placed under loads whilst a lubricant in the form of conventional transmission oil was fed onto the bearing race via an oil line. FIG. 11 illustrates the presence of the dye detected in the oil using a spectral analyser. The natural absorbance of the oil and therefore the based line in FIG. 11 illustrating the absence of the dye in the oil was at about 0.061. The presence of dye in the oil was indicated by absorbance levels above the base line. The temperature of the bearing race is shown in FIG. 11 by diamond shaped formations. The high frequency of the temperature measurements was such that the diamond formations essentially form a continuous line except for around 7500 seconds where the supply of oil to the bearing race was turned off for periods of 5 seconds, causing the temperature of the bearing race to fluctuate significantly and the increase in temperature of the bearing at approximately 5200 seconds resulted from extra load being placed on the bearing. The increase in temperature at 6000 seconds arose due to a failure in the bearing race. FIG. 11 demonstrates that the presence of the dye was only detected to a notable extent after 6500 seconds. At approximately 7500 seconds the load on the bearing race was stopped.

Those skilled in the art will appreciate that many variations and modifications may be made to the preferred embodiments and trials described above without departing from the spirit and scope of the present invention.

The claims defining the invention are as follows:

1. A system for monitoring the wear, fatigue failure, or structural health of a mechanical component or structural component; the system including:
   a) at least one sealed chamber connected to the component, wherein the or each chamber is defined by a shell or a curved wall section and a portion of the surface of the component to which the shell or curved wall section is connected, and wherein the or each chamber contains a traceable substance in which the traceable substance is confined while the chamber is intact and, in use, at least one of said chambers ruptures or opens so as to allow the traceable substance to be discharged therefrom when either one or a combination of the following occurs i) a predetermined operating temperature of the chamber equals or exceeds a threshold value or ii) a structural failure in the portion of the component that defines at least part of the chamber causes the chamber to be opened or ruptured; and
   b) a detector device for detecting the traceable substance which has been discharged from at least one of the chambers.

2. The system according to claim 1, wherein the component has a series of chambers containing traceable substances of different properties and the chambers are located at various positions on the component, such that when the traceable substances are released, the position of the component from which the traceable substance has been released is able to be identified based on the type of traceable substance released.

3. The system according to claim 1, wherein the traceable substance is discharged from the chambers(s) when the structural failure in the component is a crack that provides a passageway through which the traceable substance can be discharged from the chamber.

4. The system according to claim 1, wherein the chamber(s) include a frangible section that is temperature dependent and has a softening point so that when the operating temperature of the component equals or exceeds the softening point of the frangible section, the frangible section gives way and thereby allows the traceable material to be discharged.

5. The system according to claim 4, wherein the chamber(s) are defined by two or more wall sections joined together and that the frangible section is a frangible adhesive used to join the sections.

6. The system according to claim 5, wherein the frangible adhesive is a metallic material.

7. The system according to claim 1 wherein the mechanical component or structural component is any one of a gear, cog, bearing, drive shaft, cam surface, cylinder, cylinder head, piston, or any mechanical or structural component of a fixed or rotary wing aircraft.

8. The system according to claim 1, wherein when the mechanical component is a cog or gear, the chamber(s) are located immediately adjacent to the meshing surfaces of the teeth of the cog.

9. The system according to claim 1 wherein the system includes a housing at least partially enclosing the component such that the traceable substance is released into the housing and the detector device for detecting the traceable substance detects the presence of the traceable substance in the housing.

10. The system according to claim 1, wherein the detector device includes a window into the housing for allowing the presence of the traceable substance to be optically detected.

11. The system according to claim 1, wherein the detector device includes a chemical spectral analyser to detect the presence of the traceable substance.

12. The system according to claim 1, wherein the traceable substance is discharged into the lubricant and the detector device for detecting the traceable substance detects the presence of the traceable substance in the lubricant.

13. The system according to claim 1 including multiple components, wherein each component has at least one chamber and a different traceable substance is contained by the chamber of each respective component and the detector device for detecting the traceable substance differentiates between the different types of traceable substance, and in turn, identifies the component from which the traceable substance has been released.

14. The system according to claim 1, wherein the traceable substance includes a dye.

15. The system according to claim 1, wherein the traceable substance includes an alkyl modified naphthalocyanine.

16. The system according to claim 15, wherein the traceable substance includes vanadyl-2,11,20,29-tetra-tert-butyl-2,3-naphthalocyanine.

17. The system according to claim 12, wherein the traceable substance includes a co-solvent for increasing the solubility or miscibility of the traceable substance in the lubricant of the component.

18. The system according to claim 1, wherein the component is a part of a bearing race and the chamber(s) are mounted to the part.

19. A hardware component including at least one sealed chamber connected to the component such that the or each chamber is defined by a shell or curved wall section and a portion of the surface of the component to which the shell or curved wall section is connected, and wherein the or each chamber contains a traceable substance in which the traceable material is confined while the chamber is intact and, in use, at least one of said chambers is ruptured or opened so as to allow the traceable substance to be discharged therefrom when either one or a combination of the following occurs i) a predetermined operating temperature of the chamber equals or exceeds a threshold value, or ii) a structural failure in the portion of the component that defines at least part of the chamber, causes the chamber to be opened or ruptured.

20. The component according to claim 19, wherein the structural failure is in the form of a crack in the component through which the traceable substance can be discharged from the chamber.

21. The component according to claim 19, wherein the component has a series of chambers containing traceable substances of different properties and the chambers are located at various positions on the component, such that when the traceable substances are released, the positions of the component from which the traceable substance has been released is able to be identified based on the type of traceable substance released.

22. The component according to claim 19, wherein the chamber(s) include a frangible section that is temperature dependent and has a softening point so that when the temperature of at least part of the component equals or exceeds the softening point of the frangible section, the frangible section gives way and thereby allows the traceable substance to be discharged.

23. The component according to claim 22, wherein two or more of the chambers have different softening points and the traceable substance contained within at least two of the chambers have different properties so that detection of the respective different traceable substance is representative of the component at a particular temperature.

24. The component according to claim 22, wherein the frangible section is a metallic material.

25. The component according to claim 19, wherein the traceable substance includes a dye.

26. The component according to claim 19, wherein the traceable substance includes an alkyl modified naphthalocyanine.

27. The component according to claim 26, wherein the traceable substance includes vanadyl-2,11,20,29-tetra-tert-butyl-2,3-naphthalocyanine.

28. The component according to claim 26, wherein the traceable substance includes a co-solvent for increasing the solubility or miscibility of the traceable substance.

29. The component according to claim 19, wherein the component is a gear and the at least one chamber is located adjacent to teeth of the gear.

30. The component according to claim 19, wherein the component is a part of a bearing race and the chamber(s) are mounted to the part.

31. A method for monitoring a component such as a mechanical or structural component, the component including one or more than one sealed chamber connected to the component, wherein the or each chamber is defined by a shell or a curved wall section and a portion of the surface of the component to which the shell or curved wall section is connected, and wherein the or each chamber contains a traceable substance in which the traceable materials are confined while the chamber is intact and the or each chamber is ruptured or opened so as to allow the traceable material to be discharged therefrom when either one or a combination of the following occurs i) a predetermined operating temperature of the chamber equals or exceeds a threshold value or ii) a structural failure in the portion of the component that defines at least part of the chamber causes the chamber to be opened or ruptured, and the method including detecting the presence of the traceable substance released from the mechanical hardware component.

32. The method according to claim 31, wherein the component includes a series of chambers at different locations containing different traceable substances, and wherein the step of detecting the presence of the traceable substance involves identifying which traceable substance has been released and thereby identifying the location on the component from which the traceable substance has been released.

33. A system that monitors oil-lubricated rotating mechanical components; the system including:
  a) at least one seated chamber connected to the rotating component, wherein the or each chamber is defined by a shell or a curved wall section and a portion of the surface of the rotating component to which the shell or curved wall section is connected, and wherein the or each chamber contains a traceable substance in which the traceable substance is confined while the chamber is intact and, in use at least one of said chambers ruptures or opens so as to allow the traceable substance to be discharged therefrom when either one or a combination of the following occurs i) a predetermined operating temperature of the chamber equals or exceeds a threshold value or ii) a structural failure in the portion of the component that defines at least part of the chamber causes the chamber to be opened or ruptured; and
  b) a detector device, that detects the presence of the traceable substance when discharged from at least one of the chambers within the lubricant.

* * * * *